United States Patent [19]

Vogel et al.

[11] 4,036,838

[45] July 19, 1977

[54] PROCESS FOR THE PRODUCTION OF NITRO DERIVATIVES OF AROMATIC COMPOUNDS

[75] Inventors: Axel Vogel, Cologne; Friedrich Dürholz, Remscheid; Rudolf Sundermann; Guido Skipka, both of Leverkusen, all of Germany

[73] Assignee: Bayer Aktiengesellschaft, Leverkusen, Germany

[21] Appl. No.: 537,624

[22] Filed: Dec. 30, 1974

[30] Foreign Application Priority Data

Jan. 9, 1974  Germany .............................. 2400887

[51] Int. Cl.$^2$ ........................................... C07D 239/00
[52] U.S. Cl. ........................... 260/251 R; 260/479 R; 260/556 H; 260/471 C; 260/517; 260/590 D; 260/688; 260/645; 260/397.7 R; 260/505 R; 260/283 R; 260/543 H; 260/369; 260/558 R; 260/586; 260/607 AR; 260/465 R; 260/609 E; 260/352; 260/515; 260/471 R

[58] Field of Search ............ 260/688, 283 R, 397.7 R, 260/505 R, 543 H, 369, 558 R, 586, 607 AR, 465 R, 609 E, 352, 515, 471 R, 479 R, 556 A, 471 C, 517, 590 D, 645, 251 R

[56] References Cited

U.S. PATENT DOCUMENTS

| 2,400,287 | 5/1946 | Caesar | 260/688 |
|---|---|---|---|
| 2,826,611 | 3/1958 | Fischback et al. | 260/688 |
| 3,100,797 | 8/1963 | Harris et al. | 260/688 |
| 3,278,604 | 10/1966 | Hoffman et al. | 260/688 |
| 3,399,211 | 8/1968 | Sarett et al. | 260/688 |
| 3,459,816 | 8/1969 | Pritchett | 260/688 |
| 3,497,523 | 2/1970 | Asato | 260/688 |
| 3,711,552 | 1/1973 | Foster et al. | 260/688 |

*Primary Examiner*—Delbert R. Phillips
*Attorney, Agent, or Firm*—Burgess, Dinklage & Sprung

[57] ABSTRACT

Nitroderivates of aromatic compounds which are difficult to nitrate, can readily be obtained by nitration providing that the aromatic compound is treated with nitric acid or another nitrating agent in the presence of aliphatic or cycloaliphatic hydrocarbons monosubstituted or polysubstituted by halogen, the nitro group or an alkyl sulphonyl group, and the nitro derivative formed subsequently isolated.

17 Claims, No Drawings

PROCESS FOR THE PRODUCTION OF NITRO DERIVATIVES OF AROMATIC COMPOUNDS

This invention relates to an improved process for the production of nitro derivatives of sparingly nitratable aromatic compounds.

It has long been known that nitro derivatives of aromatic compounds which are difficult to nitrate, can be obtained by nitrating corresponding aromatic compounds. Normally the aromatic compound is dissolved in a mineral acid, preferably sulphuric acid, and nitrated by treatment with nitric acid or another nitrating agent. The nitro derivative is then normally isolated by diluting the nitration mixture with water and filtering off the nitro derivative formed.

Unfortunately, one major disadvantage of the conventional process is the use of large quantities of mineral acid as solvent which, after dilution, have to be worked up at considerable expense or they lead to effluent pollution which even today represents the most serious problem confronting industrial processes and will become an even greater problem in future. Furthermore, the solution to that problem, namely circulating the mineral acid used, gives rise to new problems in regard to the apparatus required for the process, for example in terms of corrosion prevention and reliability.

Accordingly, it is desirable to be able to carry out nitration either in the absence of any solvent or in the presence of a readily recoverable solvent.

It is also already known that the nitration of benzene derivatives can be carried out in organic solvents. However, the nitric acid undergoes very little, if any, ionisation into nitronium ions in indifferent organic solvents, which are inert under present conditions of nitration, for example chloroform, tetrachloromethane and nitromethane, so that nitration in indifferent organic solvents is selected in cases where no vigorous measures are taken, and nitration is carried out under very sparing conditions (Houben-Weyl, Methoden der organischen Chemie, 4th Edition, (1971), Stuttgart, Vol. X/1, page 484). However, even the nitration of benzene requires substantial ionisation or a high concentration of nitronium ions such as is present, for example, in sulphuric acid (loc.cit., page 485).

Negative substituents in the benzene nucleus, such as nitrile groups, nitro groups, carboxylic acid amide groups, carboxylic acid ester groups, sulphonic acid groups, sulphonamide groups, sulphochloride groups, the aldehyde group and the carboxylic acid group and also acyl groups, such as the carbonyl and sulphonyl group substituted by carbon radicals, complicate nitration of the benzene nucleus to a considerable extent and necessitate much more stringent conditions than when benzene itself is used. Thus, much higher concentrations of sulphuric acid and/or nitric acid and higher reaction temperatures are required for the nitration of aromatic carboxylic acids, such as benzoic acid and, in particular, halogen-substituted benzoic acids, than for the nitration of benzene or halogen benzenes (loc. cit. pages 619, 624). Accordingly, the use of organic solvents in the nitration of aromatic compounds negatively substituted in the nucleus appeared to be either impossible or at least unfavourable.

However, it has surprisingly been found that high yields of nitro derivatives of sparingly -nitratable aromatic compounds can readily be obtained by nitration providing that the aromatic compounds are treated with nitric acid or another nitrating agent in the presence of aliphatic or cycloaliphatic hydrocarbons monosubstituted or polysubstituted by halogen, the nitro group or an alkyl sulphonyl group, and the nitro derivative formed subsequently isolated.

In the context of the invention, sparingly nitratable aromatic compounds are, in particular, benzene and naphthalene and their derivatives which are substituted in the nucleus by at least one negatively charged substituent. Other substantially non-nitratable compounds in the context of this invention are, for example, anthraquinone, phenanthrene quinone, diphenylene sulphone, pyridine-N-oxide, pyrimidine, quinoline, quinoline-N-oxide and isoquinoline, also derivatives of these compounds.

The following are mentioned as examples of negatively charges substituents of benzene and naphthalene and derivatives thereof: the nitro group ($-NO_2$), the nitrile group ($-CN$), the aldehyde group ($-CHO$), the carboxyl group ($-COOH$), the carbalkoxy group ($-COO$-alkyl), the sulphonic acid, sulphochloride and optionally alkyl-substituted sulphonamide group ($-SO_3H$ or $-SO_3Cl$ $-SO_2NH_2$ or $-SO_2NH$-alkyl or $SO_2N(alkyl)_2$) and acyl groups.

In addition, the above-mentioned substantially non-nitratable aromatic compounds may of course be substituted in any way by one or more substituents which are inert under the nitration conditions, in which case at least one substituted hydrogen atom must of course be present.

The following are substituents which are inert under the nitration conditions: alkyl, alkoxy, acyloxy, acyl amino, carbalkoxy groups and halogen. The aromatic compounds are generally substituted by up to 2, preferably 1, of these substituents, although more than two of these substituents may also be present.

In one particular embodiment of the process according to the invention, the substantially non-nitratable aromatic compounds used are benzene derivatives corresponding to the general formula (I)

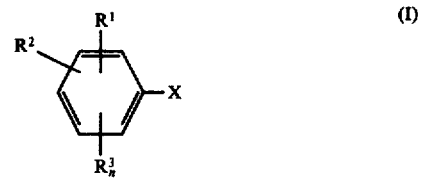

in which $R^1$ represents hydrogen, halogen, the nitro group or an optionally substituted acyl group;

$R^2$ represents hydrogen, halogen, an alkyl, alkoxy, carbalkoxy or acylamino group or the group

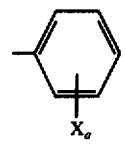

in which

X is as defined below; and a is the number 1 or 2, this group optionally being substituted by substituents which are inert under the nitration conditions;

$R^3$ represents an alkyl group;

n is the number 0, 1 or 2; where n is the number 2, the two radicals $R^3$, when they are in the o-position to one another, may together form a divalent, optionally substituted alkylene radical with 3 to 5 carbon atoms; and X represents the nitro group, nitrile group, aldehyde group, carboxyl group, carbonamide group, sulphonic acid or sulphochloride group, an optionally monoalkyl- or dialkyl-substituted sulphonamide group, an alkoxy carbonyl group, an optionally monoalkyl- or dialkyl-substituted amino carbonyl group or an acyl group.

Suitable acyl groups are alkyl carbonyl and alkyl sulphonyl groups, the phenyl carbonyl and phenyl sulphonyl group and the groups

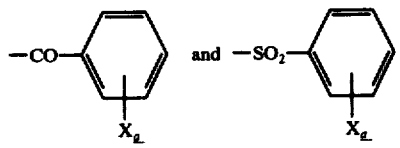

in which
X and a are as defined above.

In another particular embodiment of the process according to the invention, the sparingly nitratable aromatic compounds used are in particular benzene derivatives corresponding to the formula (IV)

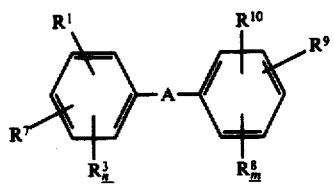

in which
$R^1$, $R^3$ and n are as previously defined;
$R^7$ represents hydrogen, halogen, an alkyl group, an alkoxy group, a carbalkoxy group or an acylamino group;
A represents a carbonyl (—CO—) or sulphone (—SO$_2$—) group; and
$R^8$ has one of the meanings above defined for the radical $R^3$;
$R^9$ has one of the meanings above defined for the radical $R^7$;
$R^{10}$ has one of the meanings above defined for the radical $R^1$;
m is the number 0, 1 or 2;
where either n and m are the numbers 1 or 2 one of each radicals $R^3$ and $R^8$ when they are in the o-positions to the radical A, may together form a single bound.

Halogens are fluorine, chlorine, bromine and iodine, preferably chlorine.

The alkyl groups are straight-chain and branched alkyl groups with up to 12 carbon atoms, preferably with up to 6 carbon atoms and more especially with from 1 to 4 carbon atoms, for example methyl, ethyl, propyl, isopropyl, butyl, isobutyl, t.-butyl, the isomeric pentyl and hexyl groups.

The scope of the term "alkyl" mentioned above also applies to the above-mentioned alkoxy, alkoxy carbonyl, alkylamino sulphonyl, dialkylamino sulphonyl, alkylamino carbonyl, dialkylamino carbonyl, alkyl carbonyl and alkyl sulphonyl radicals.

In another preferred embodiment of the process according to the invention, it is possible to obtain nitrobenzoic acids corresponding to the general formula (II),

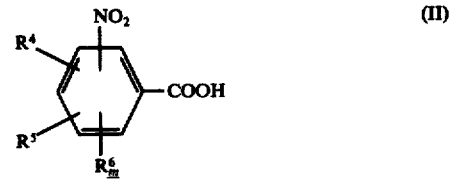

in which
$R^4$ represents hydrogen, halogen, the nitro group, a phenyl carbonyl or phenyl sulphonyl group optionally substituted by substituents which are inert under the nitration conditions or are optionally substituted acyl group;
$R^5$ represents hydrogen, halogen, nitrophenyl, an alkyl, alkoxy, carbalkoxy or acylamino group; and
$R^6$ represents an alkyl radical; and
m is the number 0, 1 or 2;
where m is the number 2, the radicals $R^6$, when they are in the o-position relative to one another, may together also form a divalent, optionally substituted alkylene radical with from 3 to 5 carbon atoms; by using benzoic acids corresponding to the general formula (III)

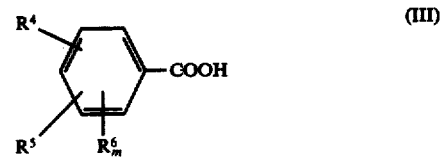

in which
$R^4$, $R^5$, $R^6$ and m are as previously defined;
as starting compounds, i.e., as the substantially non-nitratable aromatic compounds.

Substituted hydrocarbons suitable for use in the process according to the invention include aliphatic and alicyclic hydrocarbons with up to 12 carbon atoms and preferably with up to 6 carbon atoms which are monosubstituted or polysubstituted by halogen (fluorine, chlorine, bromine and iodine), the nitro group or an alkyl sulphonyl group. Substituted hydrocarbons of this kind may be based, for example, on methane, ethane, propane, butane, pentane, hexane, cyclopentane and cyclohexane. In addition to the straight-chain isomers, this exemplary list naturally includes the branched-chain isomers and alkyl-substituted cycloalkanes as well.

Preferred hydrocarbons are chlorine-substituted hydrocarbons, for example methylene chloride, chloroform, carbon tetrachloride, 1,1-dichloroethane, 1,2-dichloroethane, 1,1,2-trichloroethane, 1,1,2,2-tetrachloroethane, pentachloroethane, 1,2-dichloropropane and 1,3-dichloropropane, 1,2,3-trichloropropane-1,1,2,3- and 1,1,3,3-tetrachloropropane, 1,1,1,3,3-pentachloropropane, 1,1,1,2,3,3- and 1,1,1,2,2,3-hexachloropropane, 1,1,1,2,2,3,3- and 1,1,1,2,3,3,3-heptachloropropane, 1,2- and 1,4-dichlorobutane.

Examples of bromine-substituted hydrocarbons include methylene bromine, bromoform, terrabromomethane, 1,2-dibromoethane and 1,2-dibromopropane.

It is also possible, in the process according to the invention, to use hydrocarbons which are substituted by fluorine or simultaneously by various halogens, for example fluorotrichloromethane, difluorodichloromethane, difluorodibromoethane, 1,1,2-trifluoro-1,2,2-trichloroethane and perfluoro-1,3-dimethyl cyclohexane.

Of the hydrocarbons substituted by the nitro group, reference is made in particular to nitromethane and nitroethane.

Dimethyl sulphone and tetramethylene sulphone are mentioned as examples of hydrocarbons substituted by an alkyl sulphonyl group.

It is also possible to use mixtures of two or more of the above-mentioned substituted hydrocarbons in the process according to the invention.

The quantity of the substituted hydrocarbons (s) used in the process according to the invention may be varied within wide limits. In general, it amounts to between about 0.5 and about 25 parts by volume, preferably to between about 1 and about 10 parts by volume and, in particular, to between about 2 and about 5 parts by volume per part by weight of the substantially non-nitratable aromatic compound used.

The following compound for example may be used with advantage as benzoic acids in the process according to the invention:
benzoic acid, o-tolylic acid, m-tolylic acid, p-tolylic acid, 2,3-dimethyl benzoic acid, 2,4-dimethyl benzoic acid, 2,5-dimethyl benzoic acid, 2,6-dimethyl benzoic acid, p-isopropyl benzoic acid, o-chlorobenzoic acid, m-chlorobenzoic acid, p-chlorobenzoic acid, o-bromobenzoic acid, m-bromobenzoic acid, p-bromobenzoic acid, 2-chloro-p-tolylic acid, 2,4-dichlorobenzoic acid, 2,5-dichlorobenzoic acid, 2,6-dichlorobenzoic acid, 3-nitrobenzoic acid, 3-acetyl benzoic acid, 2-methoxy benzoic acid, 2-ethoxy benzoic acid, 4-methoxy benzoic acid, 4-ethoxy benzoic acid, 4'-nitrodiphenyl-4-carboxylic acid, 2',4'-dinitrodiphenyl-4-carboxylic acid, 5-nitronaphthalene-1-carboxylic acid.

The following are examples of other aromatic compounds which may be used as starting materials in the process according to the invention;
2-benzoyl benzoic acid, 4benzoyl benzoic acid, 3-phenyl sulphonyl benzoic acids, 4-(4-pyridyl)-benzoic acid, naphthalene-1-carboxylic acid, naphthalene-2-carboxylic acid, 4-chloronaphthalene-1-carboxylic acid, 5-chloronaphthalene-1-carboxylic acid, naphthalene-1,8-dicarboxylic acid anhydride and naphthamide; anthraquinone-1-carboxylic acid and anthraquinone-2-carboxylic acid. In addition to using the aforementioned free carboxylic acids, it is also possible to employ their derivatives, i.e., the corresponding carboxylic acid amides and carboxylic acid esters and also the nitriles upon which the free carboxylic acids are based.

The following are mentioned as examples of further aromatic compounds which may be used as starting materials in the process according to the invention:
benzaldehyde, o-chlorobenzaldehyde, m-chlorobenzaldehyde, p-chlorobenzaldehyde, 2,4-dichlorobenzaldehyde, 4-methyl benzaldehyde, 5-bromonaphthalene-1-aldehyde;
acetophenone, benzophenone, 4-methyl acetophenone, 2-chloroacetophenone, 4-chloroacetophenone, 4-nitrobenzophenone, phenanthrene quinone, 1-chloroanthraquinone, 2-chloroanthraquinone, 1,5-dichloroanthraquinone, 1-amino anthraquione, 1,5-diamino anthraquione, 2-methyl anthraquione;

methyl phenyl sulphone, chloromethylphenyl sulphone, diphenyl sulphone, 3-nitrodiphenyl sulphone, 4-chlorodiphenyl sulphone, diphenylene sulphone, 3-nitrodiphenylene sulphone; nitrobenzene, o-nitrotluene, m-nitrotoluene, p-nitrotoluene, o-chloronitrobenzene, m-chloronitrobenzene, p-chloronitrobenzene; benzene sulphochloride, p-toluene sulphochloride, p-toluene sulphonamide, naphthalene-1-sulphonic acid, naphthalene-2-sulphonic acid, anthraquinone-1-sulphonic acid, anthraquione-2-sulphonic acid, 5-chloronaphthalene-1-sulphonic acid, 8-chloronaphthalene-1-sulphonic acid, 8-acetamidonaphthalene-1-sulphonic acid, naphthalene-1,5-disulphonic acid, naphthalene-1-sulphochloride, naphthalene-2-sulphochloride;
quinonline, 2,4-dimethyl quinoline and pyridine-N-oxide.

Nitrobenzoic acids may be obtained with advantage by the process according to the invention, the following being mentioned by way of example:
3-nitrobenzoic acid, 3,5-dinitrobenzoic acid, 3-nitro-2-methyl benzoic acid, 5-nitro-2-methyl benzoic acid, 3,5-dinitro-2-methyl benzoic acid, 2-nitro-3-methyl benzoic acid, 2,6-dinitro-3-methyl benzoic acid, 3-nitro-4-methyl benzoic acid, 3,5-dinitro-4-methyl benzoic acid, 4,6-dinitro-2,3-dimethyl benzoic acid, 3-nitro-2,4-dimethyl benzoic acid, 5-nitro-2,4-dimethyl benzoic acid, 3,5-dinitro-2,4-dimethyl benzoic acid, 3,6-dinitro-2,5-dimethyl benzoic acid, 3,5-dinitro-2,6-dimethyl benzoic acid, 3-nitro-2-chlorobenzoic acid, 5-nitro-2-chlorobenzoic acid, 3,5-dinitro-2-chlorobenzoic acid, 6-nitro-3-chlorobenzoic acid, 3-nitro-4-chlorobenzoic acid, 3-nitro-2-bromobenzoic acid, 5-nitro-2-bromobenzoic acid, 3-nitro-4-bromobenzoic acid, 6-nitro-3-bromobenzoic acid, 3-nitro-2-chloro-4-methyl benzoic acid, 5-nitro-2-chloro-4-methyl benzoic acid, 5-nitro-2,4-dichlorobenzoic acid, 5-nitro-2,6-dichlorobenzoic acid, 5-nitro-3-acetyl benzoic acid, 3,5-dinitro-2-methoxy benzoic acid and 2,2',-4'-trinitrodiphenyl-4-carboxylic acid.

It is also possible by the process according to the invention to obtain, for example,
2-(3-nitrobenzoyl)-benzoic acid, 4-(3-nitrobenzoyl)-benzoic acid, 3-(3-nitrophenyl sulphonyl)-benzoic acid, 3-nitro-4-(4'-pyridyl)-benzoic acid;
5-nitronaphthalene-1-carboxylic acid, 8-nitronaphthalene-1-carboxylic acid;
3-nitrobenzaldehyde, 5-nitro-2-chlorobenzaldehye, 6-nitro-3-chlorobenzaldehyde, 5-nitro-2,4-dichlorobenzaldehyde, 3-nitro-4-methyl benzaldehyde, 5-bromo-8-nitronaphthalene-1-aldehyde; 3-nitroacetophenone, 3-nitropropiophenone, 4-nitrobenzophenone, 4,4'-dinitrobenzophenone, 3-nitro-4-methyl acetpheone, 5-nitro-2-chloroacetophenone, 3-nitro-4-chloroacetophenone, 2-nitro phenanthrene quinone, 4-nitro phenanthrene quinone, 4-nitro-1-chloroanthraquinone, 1-nitro-2-chloroanthraquinone, 4,8-dinitro-1,5-dichloroanthraquinone, 4-nitro-1-amino anthraquione, 4,8-dinitro-1,5-diamino anthraquione, 1-nitro-2-methyl anthraquinone, methyl-(3-nitrophenyl)-sulphone, chloromethyl-(3-nitrophenyl)-sulphone, 3-nitrodiphenyl sulphone, 3,3'-dinitro-diphenyl sulphone, 4-chloro-3'-nitrodiphenyl sulphone, 4-chloro-3,3'-dinitrodiphenyl sulphone, 3-nitrodiphenylene sulphone, 3,3'-dinitrodiphenylene sulphone;

m-dinitrobenzene, 2,4-dinitrotoluene, 2,6-dinitrotoluene, 3,4-dinitrotoluene, 3,5-dinitrotoluene, 2,5-dinitrotoluene, 2,4-dinitrochlorobenzene, 3,5-dinitrochlorobenzene;
3-nitrobenzene sulphochloride, 3-nitro-p-toluene sulphochloride, 5-nitronaphthalene-1-sulphonic acid, 8-nitronaphthalene-1-sulphonic acid, 8-nitro-5-chloronaphthalene-1-sulphonic acid, 5-nitro-8-chloronaphthalene-1-sulphonic acid, 3-nitro naphthalene-1,5-disulphonic acid, 5-nitronaphthalene-1-sulphochloride, 5-nitroanthraquinone-1-sulphonic acid, 8-nitroanthraquinone-1-sulphonic acid, 5-nitroanthraquinone-2-sulphonic acid, 8-nitroanthraquinone-2-sulphonic acid, 8-nitro-5-chloronaphthalene-1-sulphonic acid, 5-nitro-8-acetamino naphthalene-1-sulphonic acid; 5-nitroquinoline, 8-nitroquinoline, 6-nitro-2,4-dimethyl quinoline and 4-nitro pyridine-N-oxide.

The substantially non-nitratable aromatic compound which is used as starting compound in the process according to the invention, is hereinafter referred to in short as aromatic compound.

In general, the process according to the invention is carried out by initially introducing the aromatic compound used as starting material and the substituted hydrocarbon and carrying out the reaction with nitric acid or a nitrating agent containing nitric acid in the usual way.

There is no need for the aromatic compound used as starting material to be dissolved in the substituted hydrocarbon used. It may also be of advantage for the aromatic compound used to be merely partly or completely suspended in the substituted hydrocarbon used. This may also be of advantage for obtaining greater selectivity and/or shorter reaction times and higher volume-time yields.

Preferred nitrating agents are nitric acid or nitrating agents which, in addition to nitric acid, contain other strong mineral acids or Lewis acids, for example sulphuric acid, oleum, sulphur trioxide, phosphoric acid, polyphosphoric acid, phosphorus pentoxide, hydrogen fluoride, or alkane sulphonic acids, for example methane sulphonic acid, perfluoromethane sulphonic acid, perfluorobutane sulphonic acid. In general, up to about 50 mols, preferably up to about 15 mols and more especially about 1 to 2 mols of nitric acid are used per mol of nitro group to be introduced into the aromatic compound. In cases where, in addition to nitric acid, the nitrating agent contains others of the above-mentioned acids, the proportion of the mineral or Lewis acids added generally amounts to about 5 mols, preferably to about 3 mols and more especially to about 0.5 to 1.5 mols, based on the molar quantity of nitric acid.

In general, the nitric acid which is used contains from about 90 to 100% by weight of $HNO_3$, although it is also possible to use more dilute nitric acids with an $HNO_3$ content of up to about 50% by weight in cases where the nitrating agent also contains strong mineral or Lewis acids which are capable of binding water, for example the above-mentioned acids. Mixtures of these acids may also be present in the nitrating agent, and the nitric acid may be completely or partly replaced by nitrates, preferably ammonium and alkali nitrates.

Agents which bind the water introduced by the nitrating agent and/or the water formed during the reaction, may also be added to the reaction mixture. In general, the above-mentioned acids or mixtures thereof are used for this purpose. These agents may contain as much as 20% by weight, but preferably only up to 10% by weight, of bound water. In general, these agents are added to the reaction mixture together with the nitrating agent, optionally even in admixture, or even before or after addition of the nitrating agent. Some of them, for example sulphur trioxide, may even be added in the form of a solution in one of the organic solvents used in accordance with the invention.

The quantity of water-binding agent is best selected in accordance with the quantity of nitrating agent used, the water content and the temperature of the reaction mixture. It is preferred to use up to 10 mols and more especially up to 2 mols of the water-binding agent, based on 1 mol of nitro group to be introduced into the aromatic compound. In cases where, as is preferably the case, 1 to 2 mols of nitric acid is/are used per mol of nitro group to be introduced into the aromatic compound, the presence of a water-binding agent is generally necessary. In some cases, the aromatic compound to be nitrated may itself function as a water-binding agent, for example aromatic sulphonic acids such as naphthalene-sulphonic acid.

The reaction temperature may be varied within wide limits. In general, the reaction is carried out at temperatures in the range from $-20°$ to $+125°$ C, preferably at temperatures in the range from $0°$ to $105°$ C and more especially at temperatures in the range from $20°$ to $90°$ C.

The process according to the invention is generally carried out under normal pressure, although it may also be carried out under reduced or elevated pressure. In cases were low-boiling solvents are used in the process according to the invention, it may be essential to carry out the reaction under elevated pressure in order to attain the desired reaction temperature. In general, the process according to the invention is carried out by dissolving or suspending the aromatic compound in the organic solvent used and adding the nitrating agent used all at once, in batches or continuously and maintaining the reaction mixture at the reaction temperature selected until the reaction is complete. The water-binding agent optionally used is added beforehand, simultaneously or in admixture with or after the nitrating agent, again all at once, in batches or continuously.

It an be advantageous to terminate nitration of the aromatic compound at a conversion of about 50 to about 90% by weight of the quantity used and to separate off the nitro derivative of the aromatic compound formed as a generally substantially insoluble reaction product. A substituted hydrocarbon in which the nitro derivative formed is substantially insoluble but in which the corresponding aromatic compound used as starting material is readily soluble, may be used with advantage for this embodiment of the process. The mother liquor containing the unreacted aromatic compound may then be reused as starting solution or suspension in the process according to the invention following the addition of a correspondingly smaller quantity of the aromatic compound used. This particular embodiment of the process may be used with particular advantage for carrying out the process according to the invention in a continuous cycle.

However, the process according to the invention is preferably carried out with an almost complete conversion of the aromatic compound used. In this case, working up of the reaction mixture is generally made easier by the absence of unreacted starting material in the reaction product.

On complection of the reaction, the generally substantially insoluble reaction product may be isolated in different ways. For example, water may be added to the reaction mixture and the organic phase separated off, or the organic solvent may be distilled off and a reaction product substantially insoluble in water insolated from the aqueous phase, for example by filtration or by centrifugation. The solvent distilled off or the organic phase may be reused and recycled, optionally after working up of the organic phase, for example by distillation. The measures required for this purpose are known per se.

However, the generally substantially insoluble reaction product may also be directly isolated on completion of the reaction, for example by filtration or centrifugation washed with one of the aforementioned substituted hydrocarbons, preferably with the substituted hydrocarbon used for nitration, optionally in conjunction with a little highly concentrated nitric acid and/or water, and subsequently dried. The addition of a little highly concentrated nitric acid to the organic solvent may be advantageous insofar as, in particular, it assists in obtaining a purer reaction product. THe highly concentrated nitric acid may be added to the organic solvent used as washing agent, although it is best added to the reaction mixture on completion of nitration and before separation. Similary, a corresponding excess of highly concentrated nitric acid may be used for nitration with this purpose in mind.

The highly concentrated nitric acid used is generally nitric acid containing from 85 to 100% by weight of $HNO_3$ employed in a quantity of up to 50% by volume, preferably in a quantity of up to 40% by volume and, more especially, in a quantity of up to about 20% by volume, based on the organic solvent present.

The addition of highly concentrated nitric acid to the substituted hydrocarbon generally produces a significant increase in the solubility of the aromatic compound and/or its nitro derivative or nitro derivatives in the substituted hydrocarbon. The increase in solubility may amount to as much as 100-fold in comparison with the pure substituted hydrocarbon. It generally increases with decreasing water content in the substituted hydrocarbon/highly concentrated nitric acid mixture. It is particularly surprising in this respect that, in the mixture, the solubility of the aromatic compound or its nitro derivatives is not equal to the sum of the partial solubilities in the individual components of the mixture, instead a synergistic effect occurs so that the solubility of the mixture is generally much higher than the sum of the solubilities in the individual components. In general, the solubility of the nitro derivative (s) of the aromatic compound is greater than that of the aromatic compound itself, whereas of a mixture of aromatic compound and its nitro derivative (s) the aromatic compound is preferably dissolved, whilst the nitro derivative (s) remain (s) undissolved. Accordingly, the nitro derivative (s) of the aromatic compound is/are precipitated from an optionally prepared solution. Thus, the nitro derivative (s) may generally be separated off in a high or substantially quantitative yield and is only lightly contaminated, if at all, by unreacted starting material.

By adding a little highly concentrated nitric acid to the substituted hydrocarbon, a generally purer reaction product may also be obtained with advantage in consequence of the synergistic effect of the increase in solubility, because nitrated secondary products from the reaction are generally more readily soluble than the required reaction product and, hence, remain in the mother liquor, whilst the required reaction product, as a substantially insoluble compound, is precipitated and may be separated off in particularly pure form.

In order to obtain the aforementioned synergistic effect of the increase in solubility, from 1 to 20 mols and preferably from 2 to 10 mols, of $HNO_3$ are generally used per mol of aromatic compound to be dissolved or its nitro derivative (s).

The process described above for separating aromatic compounds from their nitro derivatives and for purifying nitro derivatives of aromatic compounds of isomers by treatment with mixtures of the above-mentioned substituted hydrocarbons and highly concentrated nitric acid, is completely independent of the process according to the invention and may also be applied to aromatic compounds and their nitro derivatives which have not been produced by the process according to the invention, i.e. by nitration as known per se in the absence of substituted hydrocarbons. However, it is preferably used in the process according to the invention as a whole and represents a preferred embodiment of the process according to the invention.

The process according to the invention may be carried out in batches, for example in a stirrer-equipped vessel, or even continuously, for example in a cascade of vessels, in a residence of dwell pipe, in a rotary installation or similar apparatus.

The process according to the invention affords significant advantages over conventional processes. Thus, the substituted hydrocarbon used in the process according to the invention may be reused either directly or, optionally, after working up, for example by distillation. The aqueous acid phase which is substantially free from dissolved secondary products may also be used reconcentrated by adding the above-mentioned water-binding agents or, for example, corresponding acid anhydrides, and recycled.

In addition, substantially pure nitro derivatives may be directly isolated by the process according to the invention, thereby eliminating the need for the otherwise necessary separate, complicated purification stage.

Above all, however, it is the use of mineral acids as solvents or diluents which is completely eliminated in the process according to the invention. Compared with prior processes, this not only saves mineral acid and, hence, costs, but it also solves the problems which would otherwise be involved in working up or eliminating quantities of acid of this order. This particular point is of a special significance in view of increasing demands for pollution control, and in itself substantiates the advance of the process according to the invention over the prior art.

Nitro derivatives of substantially non-nitratable aromatic compounds are valuable intermediate products for the production of dyes. For example, they are converted by reduction into the corresponding amino compounds which are of particular significance as coupling components for the production of azo dyes.

In the following Examples, percentages refer to weight unless otherwise stated. Concentrations of mineral acids are expressed in percent by weight, the balance being water.

EXAMPLE 1

78.25 g (0.5mol) of 4-chlorobenzoic acid were suspended in 200 ml of methylene chloride, followed by the addition with stirring at room temperature of 33.5 g (0.55 mol) of 98% nitric acid. The mixture was heated with stirring to boiling temperature, followed by the dropwise addition over a period of 1 hour at that temperature of 63.5 g of 100% sulphuric acid. After cooling to 42° C, the mixture was stirred for 2 hours at that temperature. The reaction mixture was then poured onto 300 ml of water, and the methylene chloride subsequently distilled off. The residual suspension was filtered, the residue washed with water and dried at 90° C, giving 98.4 g (97.3% of the theoretical yield) of 4-chloro-3-nitrobenzoic acid melting at 182.9° to 184.0° C with a purity of 99.5%. The content of unreacted 4-chlorobenzoic acid amounted to only about 0.1%.

EXAMPLE 2

78.25 g of 4-chlorobenzoic acid were suspended in 400 ml of 1,2-dichloroethane. 99.0 g of a mixed acid containing 35.2% of nitric acid and 64.2% of sulphuric acid were added dropwise with stirring over a period of 3 hours at 40° C. After stirring for 2 hours at that temperature, the reaction mixture was poured on to 300 ml of water. The 1,2-dichloroethane was then distilled off and the reaction product filtered off from the residual aqueous suspension, washed with water and dried at 90° C, giving 97.8 g (96.8% of the theoretical) of 4-chloro-3-nitrobenzoic acid melting at 182.9° to 184.0° C with a purity of 99.5%. The content of unreacted 4-chlorobenzoic acid amounted to only about 0.1%.

EXAMPLE 3

78.25 g of 2-chlorobenzoic acid were suspended in 400 ml of 1,2-dichloroethane, followed by the addition with stirring at room temperature of 35.5 g of 98% nitric acid. The reaction mixture was heated to 60° C, 63.5 g of 100% sulphuric acid were added dropwise with continued stirring over a period of 1 hour, followed by stirring for another 3 hours at 60° C. The reaction mixture was then poured onto 300 ml of water and the 1,2-dichloroethane distilled off. The residual aqueous suspension was filtered, the residue washed with water and dried at 90° C, giving 97.5 g (96.3% of the theoretical yield) of a mixture of 87.5% of 2-chloro-5-nitrobenzoic acid and 12% of 2-chloro-3-nitrobenzoic acid.

EXAMPLE 4

61 g of benzoic acid were suspended in 200 ml of 1,2-dichloroethane. The suspension was heated to 40° C following the addition of 38.6 g (0.60 mol) of 98% nitric acid. 63.5 g of 100% sulphuric acid were then added dropwise over a period of 2 hours at that temperature, followed by stirring for another 3 hours. After cooling to 20° C, the deposit was filtered off. The filter residue was washed four times with 4 × 25 ml of 1,2-dichloroethane and then with water, followed by drying at 90° C. 32.6 g (39% of the theoretical yield) of 3-nitrobenzoic acid were obtained in this way.

The 1,2-dichloroethane mother liquor was thoroughly stirred with 200 l ml of water and the deposit which crystallised out was filtered off. The aqueous phase of the filtrate was separated off and discarded, whilst the organic phase was concentrated by evaporation to dryness. A total of 33.5 g (32% of the theoretical) of dinitrobenzoic acid was obtained in this way.

EXAMPLE 5

61 g of benzoic acid were suspended in 200 ml of 1,2-dichloroethane, followed by the addition of 82.5 g (1.3 mols) of 99% nitric acid. After heating to 50° C, 110 g of 20% oleum were added dropwise with stirring over a period of 3 hours, followed by stirring first for 2 hours at 50° C and then for another 2 hours at 70° C. The reaction mixture was then poured on to 600 ml of water, the 1,2-dichloroethane distilled off and the solids isolated from the aqueous suspension by filtration. The yield comprised 96.5 g (91% of the theoretical yield) of dinitrobenzoic acid.

EXAMPLE 6

78.25 g of 2-chlorobenzoic acid were introduced into a mixture of 400 ml of 1,2-dichloropropane and 39 g (0.61 mol) of 98% nitric acid. The mixture was then heated with stirring to 60° C, followed by the dropwise addition over a period of 1 hour at that temperature of 62.5 g of 10% oleum. After stirring for 4 hours at the same temperature, the reaction mixture was poured on to 600 ml of water, the 1,2-dichloropropane distilled off and the solids isolated from the residual aqueous suspension by filtration, giving 96.3 g of a reaction product containing 86.3% of 2-chloro-5-nitrobenzoic acid (83% of the theoretical yield) and 12% of 2-chloro-3-nitrobenzoic acid (11% of the theoretical yield).

EXAMPLE 7

104 g (0.48 mol) of diphenylene sulphone were introduced with stirring at room temperature into a mixture of 200 ml of methylene chloride and 33.2 g (0.52 mol) of 98% by weight nitric acid. 55.5 g of 100% by weight sulphuric acid were added dropwise over a period of 3 hours at 42° C, the mixture stirred for another hour at the same temperature and then poured on to 500 ml of water. The methylene chloride was distilled off and the reaction product isolated from the residual aqueous suspension by filtration. 92% pure 3-nitrodiphenylene sulphone was obtained in a yield of 124.2 g (91% of the theoretical yield).

EXAMPLE 8

104 g (0.48 mol) of diphenylene sulphone were suspended in 300 ml of methylene chloride and dissolved with 75.5 g (1.17 mol) of 98% by weight nitric acid. 148 g of 100% by weight sulphuric acid were added dropwise under reflux with stirring over a period of 3 hours at the boiling temperature of the solution, followed by stirring for another hour at the same temperature. After cooling to 20° C, the reaction product precipitated was filtered off, washed twice with 100 ml of methylene chloride and then with water and dried at 100° C. Dinitrodiphenylene sulphone containing 93% of 3,3'-dinitrodiphenylene sulphone was obtained in a yield of 138 g (87% of the theoretical yield).

EXAMPLE 9

104 g (0.48 mol) of diphenylene sulphone were suspended in 160 ml of methylene chloride and substantially dissolved by the addition of 39.3 g (0.61 mol) of 98% by weight nitric acid. 38.9 g of 100% by weight sulphuric acid were then added dropwise with stirring over a period of 3 hours at boiling temperature, the 3-nitrodiphenylene sulphone formed began to crystallise out after only about ⅓ of the total quantity of sulphuric acid had been added. Another 140 ml of methylene chloride were then added, the mixture stirred for 30 minutes at 42° C and then cooled to 20° C. The deposit precipitated was filtered off under suction and washed first with 100 ml of methylene chloride and then with water until it was neutral, followed by drying at 100° C. 3-Diphenylene sulphone with a purity of 98% was thereby obtained in a yield of 93.4 g (73 % of the theoretical yield). The only impurity present was dinitrodiphenylene sulphone.

Another 32.5 g of a mixture of diphenylene sulphone, 3-nitrodiphenylene sulphone and 3,3'-dinitrodiphenyl sulphone, together with traces of further secondary products, were isolated from the mother liquor following the addition of 300 ml of water, removed of the methylene chloride by distillation and filtration of the residual suspension. This mixture may be used with advantage as a starting material for nitration into 3,3'-dinitrodiphenylene sulphone in accordance with Example 8.

EXAMPLE 10

68.6 g (0.5 mol) of 4-nitrotoluene were dissolved in 80 ml of methylene chloride and 38.6 g (0.6 mol) of 98% by weight nitric acid, followed by the addition with stirring over a period of 1 hour at reflux temperature of 40 g of 100% by weight sulphuric acid. After stirring under reflux for another 2 hours, the methylene chloride phase was separated off without cooling and washed three times while still hot with 3 × 200 ml of water. After the washing water had been carefully separated off, the methylene chloride was distilled off, leaving 90.2 g of dinitrotoluene containing 99% of 2,4-dinitrotoluene (98% of the theoretical yield).

EXAMPLE 11

68.6 g (0.5 mol) of 2-nitrotoluene were dissolved in 80 ml of methylene chloride and 38.6 g (0.6 mol) of 98% by weight nitric acid, followed by the addition under reflux with stirring over a period of 1 hour at boiling temperature of 40 g of 100% by weight sulphuric acid. After stirring for 2 hours under reflux, the methylene chloride phase was separated off without cooling and washed three times while still hot with 3 × 200 ml of water. After the washing water had been carefully separated off, the methylene chloride was distilled off, leaving 89.9 g (98% of the theoretical yield) of dinitrotoluene containing 99% of 2,4- and 2,6-dinitrotoluene.

EXAMPLE 12

150 g of commercial-grade 1,5-dinitronaphthalene containing 95% of 1,5-dinitronaphthalene (rest 1,8-dinitronaphthalene, trinitronaphthalenes and other impurities) were suspended in 280 ml of methylene chloride. 180 ml of 98% by weight nitric acid were run in with stirring at 40° C, followed by stirring for 15 minutes at that temperature. The undissolved fractions were separated off by filtration at 40° C and the 1,5-dinitronaphthalene precipitated from the filtrate by stirring in 80 ml of water at about 20° C. The deposit was filtered off under suction, washed first with 100 ml of methylene chloride and then with water until it was neutral, followed by drying at 100° C. 1,5-Dinitronaphthalene melting at 217° C was thus obtained in a yield of 130 g.

EXAMPLE 13

150 g of commercial-grade 1,8-dinitronaphthalene containing 93% of 1,8-dinitronaphthalene (rest 1,5-dinitronaphthalene and other impurities) were suspended in 175 ml of methylene chloride and substantially dissolved at 40° C by the addition of 75 ml of 90% by weight nitric acid. The undissolved fractions were separated off by filtration at 40° C and the 1,8-dinitronaphthalene was precipitated from the filtrate by stirring in 100 ml of water. The deposit was filtered off under suction, washed first with 100 ml of methylene chloride and then with water until it was neutral, followed by drying at 100° C. 1,8-Dinitronaphthalene melting at 169° C was thus obtained in a yield of 115 g.

EXAMPLE 14

A solution of 133 g of 98% nitric acid (1.06 mol) in 180 ml of methylene chloride was added over a period of 1 hour at 0° to 10° C to a solution of 281 g of crude naphthalene sulphonic acid (66.0% of naphthalene-1-sulphonic acid, 0.9% of naphthalene-2-sulphonic acid, 6.1% of naphthalene disulphonic acids, 4.3% of dinaphthalene sulphone and 11% of naphthalene; corresponding to 0.9 mol of naphthalene monosulphonic acids) in 380 ml of methylene chloride. After stirring for 30 minutes at 0° to 10° C, 100 ml of water were stirred into the mixture and the aqueous phase carefully separated off. The aqueous phase contained 222 g of nitronaphthalene sulphonic acids containing 27% of 5-nitronaphthalene-1-sulphonic acid (27% of the theoretical yield) and 71% of 8-nitronaphthalene-2-sulphonic acid (70% of the theoretical yield).

What we claim is:

1. A process for the production of a nitro derivative of an aromatic compound which consists essentially of contacting an aromatic compound of the formula

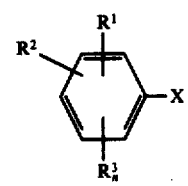

(I)

in which X represents a nitro group, nitrile group, aldehyde group, carboxyl group, carbonamide group, sulfonic or sulfochloride group, an optionally monoalkyl- or dialkyl-substituted sulfonamide group, an alkoxy carbonyl group, an optionally monoalkyl- or dialkyl-substituted amino carbonyl group or an acyl group; $R^1$ represents hydrogen, halogen, the nitro group or an optionally substituted acyl group; $R^2$ represents hydrogen, halogen, and alkyl, alkoxy, carbalkoxy or acylamino group or the group

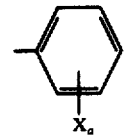

in which X is as above-defined; $a$ is 1 or 2, this group optionally being substituted by substituents which are inert under the nitration conditions; $R^3$ represents an alkyl group; and $n$ is the number 0, 1 or 2 where $n = 2$, the two radicals $R^3$ when they are in the ortho-position to one another, may together also form a divalent, optionally substituted alkylene radical with 3 to 5 carbon atoms, or a compound of the formula

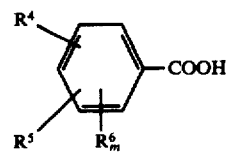

(III)

wherein R⁴ represents hydrogen, halogen the nitro group, a phenyl carbonyl or phenyl sulfonyl group optionally substituted by substituents which are inert under the nitration conditions or an optionally substituted acyl group; R⁵ represents hydrogen, halogen, nitrophenyl, an alkyl, alkoxy, carbalkoxy or acylamino group; and R⁶ represents an alkyl radical; and m is the number 0, 1 or 2; where m = 2, the two radicals R⁶, when they are in the o-position to one another, may together form a divalent, optionally substituted alkylene radical with 3 to 5 carbon atoms or a nitro derivative or an aromatic compound corresponding to the formula

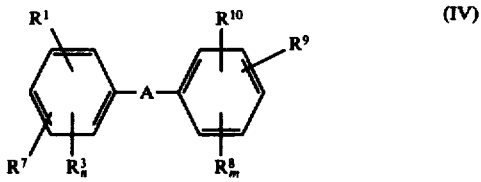

in which R¹, R³ and n are as previously defined; R⁷ represents hydrogen, halogen, an alkyl group, an alkoxy group, a carbalkoxy group or an acylamino group; A represents a carbonyl (—CO—) or sulfone (—SO₂—) group; and R⁸ has one of the meanings above-defined for the radical R³; R⁹ has one of the meanings above-defined for the radical R⁷; R¹⁰ has one of the meanings above-defined for the radical R¹; m is the number 0, 1 or 2; where either n and m are the numbers 1 or 2, one of each radicals R³ and R⁸, when they are in the o-positions to the radical A, may together form a single bound with nitric acid or a nitrating agent in the presence of an aliphatic or cycloaliphatic hydrocarbon having up to 12 carbon atoms monosubstituted or polysubstituted by halogen, the nitro group or an alkyl sulfonyl group or a compound selected from the group consisting of anthraquinone, phenathraquinone, diphenylene sulfone, pyridine-N-oxide, pyrimidine, quinoline, quinoline-N-oxide and isoquinoline, or a derivative thereof, in the presence of a mineral or Lewis acid, said process being conducted while maintaining said aliphatic or cycloaliphatic hydrocarbon in admixture with said aromatic compound until the process is substantially complete and thereafter isolating the nitro derivative of said aromatic compound.

2. A process according to claim 1 wherein the aromatic compound is one having the formula

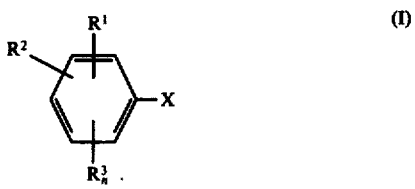

3. A process according to claim 1 wherein the aromatic compound has the formula

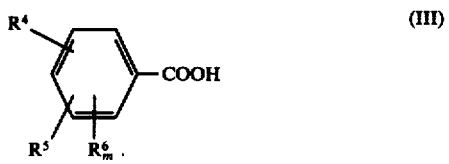

4. A process according to claim 1 wherein the aromatic compound which is reacted is one having the formula

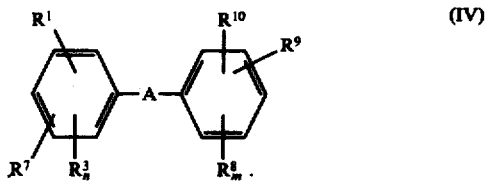

5. A process according to claim 1 wherein the mineral or Lewis acid is present in an amount up to 5 moles per mole of nitric acid.

6. A process according to claim 5 wherein the nitric acid is employed and the nitric acid is present in an amount of up to 50 moles per mole of nitro group to be inserted.

7. A process according to claim 6 wherein the nitric acid is present in an amount up to 50% by volume, based upon the amount of substituted aliphatic or cycloaliphatic hydrocarbon employed.

8. A process according to claim 1 wherein the aromatic compound is benzene or naphthalene or a derivative thereof substituted in the nucleus by at least one negatively charged substituent.

9. A process according to claim 1 wherein nitric acid or a nitrating agent is employed and the aliphatic or cycloaliphatic hydrocarbon is present in an amount of 0.5 to 25 parts by volume, based upon the weight of the aromatic compound.

10. A process according to claim 1 wherein the compound which is nitrated is anthraquinone, phenanthraquinone, diphenylene sulfone, pyridine-N-oxide, pyrimidine, quinoline, quinoline-N-oxide and isoquinoline, or a derivative thereof.

11. A process according to claim 1 wherein the nitration is carried out in the presence of methylene chloride, 1,2-dichloroethane or 1,2-dichloropropane.

12. A process according to claim 1 wherein 2 to 5 parts by volume of substituted hydrocarbon is employed per part by weight of aromatic compound.

13. A process according to claim 1 wherein, optionally after intermediate isolation, the nitro derivative formed is treated with an aliphatic or cycloaliphatic hydrocarbon having up to 12 carbon atoms monosubstituted or polysubstituted by halogen, the nitro group or an alkyl sulfonyl group.

14. A process according to claim 13 wherein highly concentrated nitric acid is added to the hydrocarbon.

15. A process according to claim 14 wherein the highly concentrated nitric acid contains from 85 to 100% by weight of HNO₃.

16. A process according to claim 1 wherein the highly concentrated nitric acid is employed and the same is added in the quantity of up to 20% by volume, based on the aliphatic or cycloaliphatic hydrocarbon.

17. A process according to claim 1 wherein from 1 to 20 moles of HNO₃ are used per mole of undesirable secondary product.

* * * * *